United States Patent [19]

Pallos et al.

[11] 4,230,874
[45] Oct. 28, 1980

[54] N-(BENZENESULFONYL) CARBAMATES-HERBICIDAL ANTIDOTES

[75] Inventors: Ferenc M. Pallos, Walnut Creek; Edmund J. Gaughan, Berkeley, both of Calif.

[73] Assignee: Stauffer Chemical Company, Westport, Conn.

[21] Appl. No.: 721,721

[22] Filed: Sep. 13, 1976

Related U.S. Application Data

[63] Continuation-in-part of Ser. No. 619,114, Oct. 2, 1975, abandoned.

[51] Int. Cl.³ ............................................. C07C 147/13
[52] U.S. Cl. .................................. 560/12; 260/340.7; 260/465 D; 546/342; 71/70; 71/76; 71/77; 71/88; 71/93; 71/94; 71/98; 71/100; 71/103
[58] Field of Search ..................... 260/470; 71/103, 98

[56] References Cited

U.S. PATENT DOCUMENTS

| | | | |
|---|---|---|---|
| 3,326,967 | 6/1967 | Ratz et al. .............................. | 71/103 |
| 3,377,375 | 4/1968 | Stephens ............................... | 260/470 |
| 3,512,955 | 5/1970 | Stephens ............................... | 71/103 |
| 3,779,760 | 12/1973 | Stephens ............................... | 71/103 |
| 3,790,619 | 2/1974 | Edamura et al. ..................... | 260/470 |
| 3,920,727 | 11/1975 | Metzger et al. ....................... | 260/470 |
| 3,978,228 | 8/1976 | Yoshinaga et al. ................... | 71/103 |

OTHER PUBLICATIONS

Yale et al., "1–Alkyl–3($\alpha,\alpha,\alpha$-trifluorotolyl sulfonyl)ureas" (1960) CA 55 pp. 2542–2543 (1961).
Boehringer et al., "Sulfonylurethans" (1966) CA 66 No. 55245b (1967).
Hirooka et al., "Synthesis and Reactions of etc.," (1970) Ca 73 No. 14369n (1970).
Farbwerke Hoechst A.G. "Sulfonylurethane" (1959) CA 55 pp. 4433-4434 (1961).

*Primary Examiner*—Glennon H. Hollrah
*Attorney, Agent, or Firm*—Harry A. Pacini

[57] ABSTRACT

N-(substituted benzenesulfonyl) carbamates as new compositions of matter useful as active herbicidal antidotes to protect against and decrease crop injury when used with a thiocarbamate herbicide when applied in various methods; improved herbicidal compositions and utility of said compositions to protect against and decrease phytotoxic crop injury when employing thiocarbamate herbicides and a two-part herbicide system comprising a first-part of one or more thiocarbamate herbicide and a second part of an effective antidote therefor compound said antidote compounds of the class N-benzene sulfonyl carbamates having the formula

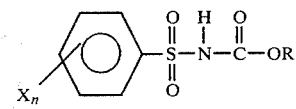

wherein X is hydrogen, bromo, chloro, methoxy, trifluoromethyl, and methyl; n is an integer from 1 to 3 inclusive, provided that when X is bromo, trifluoromethyl, or methoxy, n is 1; and R is selected from alkyl, haloalkyl wherein halo is chloro or fluoro, alkenyl; haloalkenyl and wherein halo is chloro, alkynyl, trifluoroacetamidomethyl, dialkylamino cyanoalkylthioalkyl, phosphonomethyl, lower alkyl substituted phenyl, 4-chlorophenylthiomethyl, alkoxyalkyl, alkylthioalkyl, cyanoalkyl, alkoxycarbonylalkyl, formamidoalkyl, alkoxycarbonylalkenyl, alkylcarbonylalkyl, 1,3-dioxacyclohexane-5,5-methylene, phenyl, chlorophenyl, benzyl, 4-chlorobenzyl, 4-methoxybenzyl, 3-pyridylmethyl, phenoxyethyl, 3-phenylpropyn-2-yl, methylthioacetimino, acetone imino and benzaldimino.

3 Claims, No Drawings

N-(BENZENESULFONYL) CARBAMATES-HERBICIDAL ANTIDOTES

This Application is a continuation-in-part application of copending U.S. Ser. No. 619,114 filed Oct. 2, 1975 now abandoned.

BACKGROUND OF THE INVENTION

While many herbicides are immediately toxic to a large number of weed pests, it is known that the effect of many herbicides upon important plant cultivations is either non-selective or not adequately selective. Thus, many herbicides damage not only the weeds to be controlled but, to a greater or lesser extent, the desirable cultivated plants as well. This holds true for many herbicidal compounds which have been commercially successful and are commercially available. These herbicides include types such as triazines, urea derivatives, halogenated acetanilides, carbamates, thiocarbamates and the like. Some examples of these compounds are described in U.S. Pat. Nos. 2,913,327, 3,037,853, 3,175,897, 3,185,720, 3,198,786 and 3,582,314.

The side effect of injury to a cultivated crop by various herbicides is particularly inconvenient and unfortunate. When used in the recommended amounts in the soil to control broadleaf weeds and grasses, serious malformation or stunting of the crop plants sometimes result. This abnormal growth in the crop plants sometimes result. This abnormal growth in the crop plants results in loss of crop yield. The search continues for good selective herbicides.

Previous attempts are described to overcome this problem. The treatment of the crop seed with certain "hormonal" antagonistic agents prior to planting is described; see U.S. Pat. Nos. 3,131,509 and 3,564,768. The protective agents, as well as the herbicide, in these prior processes are largely specific to certain cultivated plant species or in the nature of the antagonistic agents. The prior antagonistic agents have not been notably successful. The aforementioned patents specifically exemplify and describe the treatment of seeds employing compounds of a different chemical class, not suggestive of the present invention.

U.S. Pat. Nos. 3,799,760 and 3,933,894, and East German Patent DL No. 74982 disclose certain N-benzenesulfonyl carbamate compounds, disclosed herein. Also, in Berichte, Vol. 37 at Page 699, certain compounds are specifically disclosed. None of these references anticipate or make obvious the utility of the compounds as herbicidal antidotes for thiocarbamate herbicides, in particular for S-n-propyl N,N-di-n-propylthiocarbamate. None of the references anticipate or make obvious the improved herbicidal compositions for use employing N-benzenesulfonyl carbamates and an active thiocarbamate herbicide, particularly S-n-propyl N,N-di-n-propylthiocarbamate.

DESCRIPTION OF THE INVENTION

It has been discovered that cultivated crop plants, can be protected against injury by thiocarbamate-type herbicides, and said injury can be decreased when the thiocarbamate-type herbicides, each alone or in mixtures or combination with other compounds, are applied in a variety of ways. Further, as an alternative effect, the tolerance of the plants, to these herbicides, can be substantially increased by adding to the soil an antidote compound of the type N-(substituted benzenesulfonyl) carbamates, therefore, the present invention also includes a two-part herbicide system comprising a first part of one or more thiocarbamate herbicide and a second part of an effective antidote compound therefore, said antidote compounds corresponding to the following formula

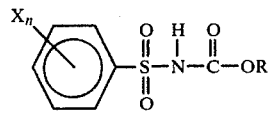

in which X is hydrogen, bromo, chloro, methoxy, trifluoromethyl, and methyl; n is an integer from 1 to 3 inclusive, provided that when X is bromo, trifluoromethyl, or methoxy, n is 1; and R is selected from alkyl having 1 to 4 carbon atoms, inclusive, haloalkenyl having 3 to 6 carbon atoms, inclusive and wherein halo is chloro from 1 to 4, inclusive, alkynyl having 3 to 6 carbon atoms, inclusive, trifluoracetamidomethyl, dialkylamino having a total of 2 to 8 carbon atoms, inclusive, cyanoalkylthioalkyl having a total of 3 to 6 carbon atoms, inclusive, phosphonomethyl, lower alkyl substituted phenyl said lower alkyl each having 1 to 4 carbon atoms, inclusive, 4-chlorophenylthiomethyl, alkoxyalkyl having 2 to 6 carbon atoms, inclusive, alkylthioalkyl having 2 to 6 carbon atoms, inclusive cyanoalkyl having 2 to 6 carbon atoms, inclusive, alkoxycarbonylalkyl having 3 to 7 carbon atoms, inclusive, formamidoalkyl having 2 to 6 carbon atoms, inclusive, alkoxycarbonylalkenyl having 4 to 7 carbon atoms, inclusive, alkylcarbonylalkyl having 3 to 6 carbon atoms, inclusive, 1,3-dioxacyclohexane-5,5-methyl methylene, phenyl, chlorophenyl, benzyl, 4-chlorobenzyl, 4-methoxybenzyl, 3-pyridylmethyl, phenoxyethyl, 3-phenylpropyn-2-yl, methylthioacetimino, acetone imino and benzaldimino.

Certain compounds disclosed herein are considered new compositions of matter and correspond to the following formula

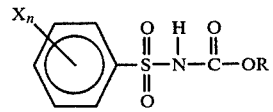

in which X is hydrogen, bromo, chloro, methoxy, trifluoromethyl, and methyl; n is an integer from 1 to 3 inclusive, provided that when X is bromo, trifluoromethyl, or methoxy, n is 1; and R is selected from haloalkyl having 2 to 6 carbon atoms, inclusive, wherein halo is chloro or fluoro from 1 to 6, inclusive, haloalkenyl having 3 to 6 carbon atoms, inclusive and wherein halo is chloro from 1 to 4, inclusive, dialkylamino having a total of 2 to 8 carbon atoms, inclusive, cyanoalkylthioalkyl having a total of 3 to 6 carbon atoms, inclusive, phosphonomethyl, trifluoroacetamidomethyl, lower alkyl substituted phenyl said lower alkyl each having 1 to 4 carbon atoms, inclusive, 4-chlorophenylthiomethyl, alkoxyalkyl having 2 to 6 carbon atoms, inclusive, alkylthioalkyl having 2 to 6 carbon atoms, inclusive cyanoalkyl having 2 to 6 carbon atoms, inclusive, alkoxycarbonylalkyl having 3 to 7 carbon atoms, inclusive, formamidoalkyl having 2 to 6 carbon atoms, inclusive, alkoxycarbonylalkenyl having 4 to 7 carbon atoms, inclusive, alkylcarbonylalkyl having 3 to 6 carbon atoms, inclusive, 1,3-dioxacyclohexane-5,5-methyl methylene, chlorophenyl, 4-chlorobenzyl, 4-methoxybenzyl, 3-pyridylmethyl, phenoxyethyl, 3-phenylpropyn-2-yl, methylthioacetimino, acetone imino and benzaldimino.

Also provided that when X is trifluoromethylyl and n is 1, then R can be alkyl having 1 to 4 carbon atoms inclusive, alkenyl having 3 to 6 carbon atoms, inclusive, and alkynyl having 3 to 6 carbon atoms, inclusive.

In the above descriptions, the following embodiments are intended for the various substituent groups: For R, haloalkyl preferably includes those members which contain from 1 to 6 carbon atoms, inclusive, in both straight chain and branched chain configurations and the term "halo" includes chloro, bromo and fluoro, as mono, di, tri, tetra, or hexa substitutions that is from 1 to 6 halo substituents. As exemplary of the alkyl portion within the preferred embodiment are the following: Methyl, ethyl, n-propyl, isopropyl, n-butyl, sec.-butyl, isobutyl and tert.-butyl. For R, alkynyl preferably includes those members which contain from 3 to 6 carbon atoms and at least one acetylenic or triple bond such as in propargyl (propynyl), 2-butynyl, 3-butynyl, 1,1-dimethyl-3-butynyl, and the like. Chloroalkenyl preferably includes those members which contain from 3 to 6 carbon atoms, inclusive, and at least one olefinic double bond. Other substituent groups are as indicated in carbon content in the above description.

As an alternative mode of action, the compounds of this invention may interfere with the normal herbicidal action of the thiocarbamate-type and other herbicides to render them selective in their action. The observation noted with the presence of the herein described antidote is a decrease in phytotoxity with respect to various crops, otherwise observed when various thiocarbamate herbicides are used for weed control. Whichever mode of action is present, the corresponding beneficial and desirable effect is the continued herbicidal effect of the thiocarbamate with the accompanying decreased herbicidal effect on desired crop species. This advantage and utility will become more apparent hereinafter.

Therefore, the terms, "herbicide antidote" or "antidotal amount", is meant to describe that effect which tends to counteract the normal injurious herbicidal response that the herbicide might otherwise produce. Whether it is to be termed a remedy, interferant, protectant, antagonist or the like, will depend upon the exact mode of action. The mode of action is varied, but the effect, which is desirable, is the result of the method of treating the seed, soil or furrow in which a crop is planted. Hitherto, there have been no systems which have been satisfactory for this purpose.

The compounds of this invention represented by the above formulas can be prepared by several different procedures depending upon the starting materials.

One general method for preparing N-benzenesulfonyl alkynyl carbamates is the reaction of an appropriate alkynol with benzenesulfonyl isocyanate. More particularly, the reaction is performed in the presence of a solvent such as benzene or chloroform with catalytic amounts of triethylamine and dibutyl tin dilaurate. In some instances, a catalyst is not required. After the reaction is complete, the product is recovered by filtration or evaporation of the solvent. If necessary, the product can be recrystallized from a suitable solvent.

A general method for preparing N-benzenesulfonyl alkyl carbamates is the reaction of an appropriate benzenesulfonamide with an alkyl chloroformate in the presence of a catalyst, such as potassium carbonate. A solvent is normally employed to facilitate the reaction and aid in the work-up of the product. After filtration, extraction and drying, the product can be purified further by trituration with hexane or recrystallization from a suitable solvent. In most instances, the structure was confirmed by infrared, nuclear magnetic resonance or mass spectroscopy.

The compounds of the present invention and their preparation are more particularly illustrated by the following examples. Following the examples of preparation is a table of compounds which are prepared according to the procedures described herein. Compound numbers have been assigned to them and are used for identification throughout the balance of the specification.

EXAMPLE I

Preparation of 2-butyn-1-yl p-toluenesulfonyl carbamate

To a solution of 2-butyn-1-ol, 1.75 g. (0.025 mole) in 25 ml. chloroform was added slowly 4.9 g. (0.025 mole) p-toluenesulfonyl isocyanate. An exothermic reaction resulted. The product was removed by evaporating the solvent. There was obtained a yield of 6.4 g. of the title compound, m.p. 85°–90° C.

EXAMPLE II

Preparation of 2-bromopropyl p-toluenesulfonyl carbamate

In a similar procedure as described in Example 1, 2-bromo-1-propanol, 3.4 g. (0.025 mole) in 25 ml. chloroform and 4.9 g. (0.025 mole) p-toluenesulfonylisocyanate were reacted. After a similar work-up to remove the solvent, there was obtained a yield of 8.4 g. of the title compound, $n_D^{30}$ 1.5375.

EXAMPLE III

Preparation of hexafluoroisopropyl p-toluenesulfonyl carbamate

In a similar procedure as described in Example 1, symhexafluoroisopropanol, 4.2 g. in 25 ml. chloroform and 4.9 g. (0.025 mole) p-toluenesulfonylisocyanate were reacted with 2 drops of triethylamine as catalyst. After a similar work-up to remove the solvent, there was obtained a yield of 8.9 g. of the title compound, m.p. 69°–75° C.

EXAMPLE IV

Preparation of N-(p-chlorobenzenesulfonyl)-propargyl carbamate

To a solution of 1.7 g. (0.03 mole) of propargyl alcohol in 20 ml. of benzene containing one drop of triethylamine and one drop of dibutyl tin dilaurate was added a solution of 6.5 g. (0.03 mole) p-chlorobenzenesulfonyl isocyanate in 25 ml. benzene. The reaction was exothermic and the temperature was allowed to rise to 30° C. The mixture was stirred several hours at room temperature and the precipitated solid was filtered and washed with a small amount of hexane and dried. There was obtained a yield of 8.0 g. (98% of theory) of the title compound, m.p. 106°–108° C. A pure sample melted at 120.5°–121° C. The structure was confirmed by infrared, nuclear magnetic resonance, and mass spectroscopy.

EXAMPLE V

Preparation of N-(p-chlorobenzenesulfonyl)-ethyl carbamate p-Chlorobenzenesulfonamide (6.1 g., 0.032 mole), potassium carbonate (10.8 g., 0.078 mole), and ethyl chloroformate (3.7 g., 0.034 mole) in 40 ml. of acetone were stirred and refluxed for two hours. During the heating period the mixture became thick and was diluted with another 30 ml. of acetone. The cooled mixture was poured into 150 ml. of water and filtered through Celite. The filtrate was acidified with hydrochloric acid with cooling (pH about 2) and the product extracted with benzene. The extract was washed with water and dried over anhydrous magnesium sulfate. Removal of the solvent left the title compound as a solid. There was obtained a yield of 5.5 g. (65% of theory) of the title compound, m.p. 85°–90° C. The structure was confirmed by IR.

EXAMPLE VI

Preparation of N-(p-methoxybenzenesulfonyl)-ethyl carbamate p-Methoxybenzenesulfonamide (5.0 g., 0.032 mole) potassium carbonate (10.8 g., 0.078 mole), and ethyl chloroformate (3.7 g., 0.034 mole) in 40 ml. of acetone were refluxed for 2.5 hours. The product was worked up in a similar manner as in Example V. There was obtained a yield of 3.9 g. (47% of theory) of the title compound, m.p. 110°–116° C.

The following is a table of the compounds which are prepared according to the aforementioned procedures. Compound numbers have been assigned to them and are used for identification throughout the balance of the specification.

TABLE I

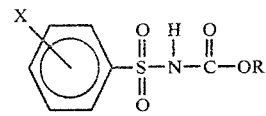

| Compound Number | X | R | m.p. °C. or $n_D^{30}$ |
|---|---|---|---|
| 1 | 4-CH$_3$ | CH(CH$_3$)$_2$ | sticky* |
| 2 | 4-OCH$_3$ | C$_2$H$_5$ | 110–116 |
| 3 | 4-Cl | C$_2$H$_5$ | 85–90 |
| 4 | 4-CH$_3$ | CH(CF$_3$)$_2$ | 69–75 |
| 5 | 4-CH$_3$ | CH$_2$CH$_2$Br | 1.5460 |
| 6 | 4-CH$_3$ | CH$_2$CH$_2$Cl | 1.5348 |
| 7 | 4-CH | CH$_2$CHBrCH$_3$ | 1.5375 |
| 8 | 4-CH$_3$ | CH$_2$CF$_3$ | 120–125 |
| 9 | 4-CH$_3$ | CH$_2$CH(Cl)CH$_2$Cl | semi-solid* |
| 10 | 4-CH$_3$ | CH$_2$C(CH$_3$)ClCH$_2$Cl | 1.5640 |
| 11 | 4-Cl | CH$_2$CHCl$_2$ | 114–115 |
| 12 | 4-Cl | CH$_2$CF$_3$ | 142–145 |
| 13 | 4-Cl | CH(CF$_3$)$_2$ | 83–87 |
| 14 | 4-Br | CH$_2$CH$_2$Cl | semi-solid* |
| 15 | 4-Cl | CH$_2$CH(Cl)CH$_2$Cl | semi-solid* |
| 16 | 4-Cl | CH$_2$CH$_2$Br | 92–98 |
| 17 | 4-CH$_3$ | CH$_2$C≡CCH$_3$ | 85–90 |
| 18 | 4-Cl | CH$_2$C≡CH | 106–108 |
| 19 | 4-Cl | CH$_2$CH$_2$C≡CH | 102–104 |
| 20 | 4-Cl | C(CH$_3$)$_2$CH$_2$C≡CH | 108–110 |
| 21 | 4-Cl | CH$_2$C≡CCH$_3$ | 141–142 |
| 22 | 4-CH$_3$ | CH$_2$CH$_2$C≡CH | glass* |
| 23 | H | CH$_2$C≡CH | 78–80 |
| 24 | H | CH$_2$C≡CCH$_3$ | 114–116 |
| 25 | H | CH$_2$CH$_2$C≡CH | semi-solid* |
| 26 | H | CH$_2$CCl=CH$_2$ | semi-solid* |
| 27 | 4-Br | CH$_2$C≡CH | 124–125 |
| 28 | 4-Br | CH$_2$C≡CCH$_3$ | 134–135 |
| 29 | H | CH$_2$CF$_3$ | 93–95 |
| 30 | H | CH$_2$CH$_2$Cl | semi-solid* |

TABLE I-continued

| Compound Number | X | R | m.p. °C. or $n_D^{30}$ |
|---|---|---|---|
| 31 | H | CH$_2$CHCl$_2$ | semi-solid* |
| 32 | H | CH$_3$ | 127–130 |
| 33 | H | C$_2$H$_5$ | 1.5003 |
| 34 | H | n-C$_3$H$_7$ | 1.4942 |
| 35 | H | i-C$_3$H$_7$ | 1.4952 |
| 36 | H | CH$_2$CCl$_3$ | 121–122 |
| 37 | H | CH$_2$CF$_2$CF$_2$H | 94–97 |
| 38 | H | CH$_2$CH=CH$_2$ | 1.5175 |
| 39 | 4-CH$_3$ | CH$_2$CCl$_2$CH$_2$Cl | 1.5300 |
| 40 | 4-CH$_3$ | CH$_2$CH=CH$_2$ | 1.5375 |
| 41 | 4-CH$_3$ | CH$_2$C(CH$_3$)=CH$_2$ | 1.5300 |
| 42 | 4-CH$_3$ | CH$_2$C(Cl)=CH$_2$ | 1.5340 |
| 43 | 4-CH$_3$ | CH$_2$C≡CH | 1.5384 |
| 44 | 4-CH$_3$ | C(CH$_3$)$_2$C≡CH | glass* |
| 45 | 4-CH$_3$ | C(CH$_3$)$_2$C≡CCH$_3$ | glass* |
| 46 | 4-CH$_3$ | CH(i-C$_3$H$_7$)C≡CH | glass* |
| 47 | 4-CH$_3$ | N(C$_2$H$_5$)$_2$ | semi-solid* |
| 48 | 4-CH$_3$ | CH$_2$NHC(O)CF$_3$ | sticky |
| 49 | 4-CH$_3$ | CH$_2$P(O)(OH)$_2$ | semi-solid |
| 50 | 4-CH$_3$ | CH$_2$S—⟨C$_6$H$_4$⟩—Cl | 65–70 |
| 51 | 4-Cl | CH$_3$ | 127–130 |
| 52 | 4-Cl | n-C$_3$H$_7$ | 1.5111 |
| 53 | 4-Cl | C$_2$H$_4$Cl | semi-solid |
| 54 | 4-Cl | CH$_2$CH=CH$_2$ | 1.5262 |
| 55 | 4-Cl | CH$_2$C(Cl)=CH$_2$ | 89–92 |
| 56 | 4-Cl | CH$_2$C(O)OC$_2$H$_5$ | 1.4783 |
| 57 | 4-Cl | phenyl | 101–104 |
| 58 | 4-Cl | CH$_2$-pyridyl | 174–176 |
| 59 | 4-Cl | CH$_2$C≡C-phenyl | 109–111 |
| 60 | 3-CF$_3$ | C$_2$H$_5$ | 59–63 |
| 61 | 3-CF$_3$ | CH$_2$CF$_3$ | 91–96 |
| 62 | 3-CF$_3$ | CH$_2$CH=CH$_2$ | 66–70 |
| 63 | 3-CF$_3$ | CH$_2$C≡CH | 76–77 |
| 64 | 3,4-diCl | C$_2$H$_5$ | 100–102 |
| 65 | 2-CF$_3$ | C$_2$H$_5$ | 129–131 |
| 66 | 3-Cl | C$_2$H$_5$ | 1.5155 |
| 67 | 3-Cl | CH$_2$CF$_3$ | 108–110 |
| 68 | 3-Cl | CH$_2$CH=CH$_2$ | 58–61 |
| 69 | 3-Cl | CH$_2$C≡CH | 73–76 |
| 70 | 3-Cl | CH$_2$C≡CCH$_3$ | 95–97 |
| 71 | 2,4,6-CH$_3$ | C$_2$H$_5$ | 159–160 |
| 72 | 2,4,6-CH$_3$ | i-C$_3$H$_7$ | 112–114 |
| 73 | 2,4,6-CH$_3$ | CH$_2$CF$_3$ | 159–162 |
| 74 | 2,4,6-CH$_3$ | CH$_2$CCl$_3$ | 139–141 |
| 75 | 2,4,6-CH$_3$ | CH$_2$C≡CH | 150.151 |
| 76 | 2,4,6-CH$_3$ | 4-Cl-phenyl | 131–132 |
| 77 | 2,4,6-CH$_3$ | —N=CH-phenyl | 120–122 dec. |
| 78 | 4-CH$_3$ | C$_2$H$_4$F | 1.5022 |
| 79 | 4-CH$_3$ | C$_2$H$_4$SC$_2$H$_4$CN | 1.5482 |
| 80 | 4-CH$_3$ | 3,4-di-CH$_3$-phenyl | 80–82 |
| 81 | 4-CH$_3$ | —N=C(CH$_3$)SCH$_3$ | 145–147 |
| 82 | 4-Cl | t-C$_4$H$_9$ | 119–122 |
| 83 | 4-Cl | C$_2$H$_4$F | 1.5192 |
| 84 | 4-Cl | CH$_2$CF$_2$CF$_2$H | 82.85 |
| 85 | 4-Cl | C(CH$_3$)(C$_2$H$_5$)C≡CH | 122–124 |
| 86 | 4-Cl | C$_2$H$_4$OC$_2$H$_5$ | semi-solid* |
| 87 | 4-Cl | C$_2$H$_4$SC$_2$H$_5$ | 1.5360 |
| 88 | 4-Cl | C(CH$_3$)$_2$CN | 68–71 |
| 89 | 4-Cl | C$_2$H$_4$C(O)CH$_3$ | 94–98 |

TABLE I-continued $$\underset{X}{\bigcirc}\overset{O}{\underset{\underset{O}{\overset{\|}{S}}}{\|}}-\overset{H}{\underset{|}{N}}-\overset{O}{\overset{\|}{C}}-OR$$

| Compound Number | X | R | m.p. °C. or $n_D^{30}$ |
|---|---|---|---|
| 90 | 4-Cl | 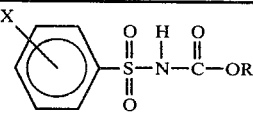 | viscous semi-solid* |
| 91 | 4-Cl | CH(CH$_3$)C(O)OC$_2$H$_5$ | 1.4950 |
| 92 | 4-Cl | C$_2$H$_4$NHC(O)H | 154–157 dec. |
| 93 | 4-Cl | C(CH$_3$)=CHC(O)OC$_2$H$_5$ | 1.5100 |
| 94 | 4-Cl | 4-Cl-phenyl | 159–160 |
| 95 | 4-Cl | 2-Cl-phenyl | 77–80 |
| 96 | 4-Cl | 3,4-diCH$_3$-phenyl | 100–103 |
| 97 | 4-Cl | 3,4,5-tri-CH$_3$-phenyl | 1.5473 |
| 98 | 4-Cl | 2-i-C$_3$H$_7$-phenyl | 1.5471 |
| 99 | 4-Cl | 3,5-di-i-C$_3$H$_7$-phenyl | 1.5415 |
| 100 | 4-Cl | 3-t-C$_4$H$_9$-phenyl | oil* |
| 101 | 4-Cl | benzyl | 98–101 |
| 102 | 4-Cl | 4-Cl-benzyl | 138–139 |
| 103 | 4-Cl | 4-CH$_3$O-benzyl | 119–122 |
| 104 | 4-Cl | phenoxy-CH$_2$CH$_2$ | 98–99 |
| 105 | 4-Cl | —N=C(CH$_3$)$_2$ | 161–162 |
| 106 | 4-Cl | —N=C(CH$_3$)SCH$_3$ | 125–128 |
| 107 | 4-Cl | —N=CH-phenyl | 120–124 dec. |

*Structure confirmed by either infrared or nuclear magnetic resonance spectroscopy.

The herbicides indicated in the tables and elsewhere are used are rates which produce effective control of undesirable vegetation. The range of rates employed herein produce representative results within the recommended amounts set forth by the supplier. Therefore, the weed control in each instance is commercially acceptable within the desired or recommended amount.

It is clear that the class of herbicidal agent described and illustrated herein is characterized as effective herbicide exhibiting such activity. The degree of this herbicidal activity varies among specific compounds and among combinations of specific compounds within the class. Similarly, the degree of activity to some extent varies among the species of plants to which a specific herbicidal compound or combination may be applied. Thus, selection of a specific herbicidal compound or combination to control undesirable plant species readily may be made. Within the present invention, the prevention of injury to a desired crop species in the presence of a specific compound or combination may be achieved. The beneficial plant species which can be protected by this method is not intended to be limited by the specific crops employed in the examples.

The herbicidal compound employed in the utility of this invention is an active thiocarbamate herbicide of a general type. That is, it is a member of the class of herbicidally active compounds effective against a wide range of plant species with no discrimination between desirable and undesirable species. The method of controlling vegetation comprises applying an herbicidally effective amount of the herein described herbicidal compound to the area or plant locus where control is desired. The compositions as set forth in this invention include those wherein the antidote is as described above and the preferred active herbicidal compound is selected from the class of thiocarbamate herbicides and includes the following as representative members, S-ethyl dipropyl thiocarbamate, S-ethyl diisobutyl thiocarbamate, S-propyl di-n-propyl thiocarbamate, S-ethyl cyclohexyl ethyl thiocarbamate, S-ethyl-hexahydro-1H-azeplne-1 carbothioate, 2,3,3-trichloroallyl N,N-diisopropyl thiocarbamate, S-isopropyl-1-(5-ethyl-2-methylpiperidine) carbothioate; alone and with various combinations thereof and with such other classes of herbicidal compounds, as triazines, for example, 2-chloro-4-ethylamino-6-isopropylamino-s-triazine, 2-chloro-4,6-bis(ethylamino)-3-triazine, 2(4-chloro-6-ethylamine-s-triazine-2-yl amino)-2-methylpropionitrile, 2-chloro-4-cyclopropylamino-6-isopropylamino-s-triazine.

As an embodiment within the scope of the present invention is a two part or package herbicide system comprising a first part of one or more thiocarbamate herbicide and a second part of an antidote compound therefore it is understood that the antidote compound is used in an effective amount to render the two-part herbicide system selective in decreasing phytotoxic effects to desired or beneficial crops and yet phytotoxic to the undesirable or unwanted vegetation. Thus the soil treated by such a system becomes extremely useful and desirable, allowing previously injured crops to be planted in said treated soil, otherwise injured by the herbicide when used alone. Hence, soil treated with herbicide and antidote is described herein is beneficial, desirable and useful.

An herbicide as used herein means a compound which controls or modifies the growth of vegetation or plants. Such controlling or modifying effects include all deviations from natural development; for example, killing, retardation, defoliation, desiccation, regulation, stunting, tillering, stimulation, dwarfing and the like. By "plants", it is meant germinant seeds, emerging seedlings and established vegetation including the roots and above-ground portions.

Evaluation Procedures

Flats to be used for growing the crops and weed species were filled with loamy sand soil. Stock solutions of the herbicide and each candidate antidote were prepared as follows:

A. Herbicide—S-n-propyl N,N-di-n-propyl thiocarbamate—VERNAM® 6E—1560 mg. of VERNAM 6E was diluted in 250 ml. of water so that 5 ml. applied to a flat is equivalent to 6 lb/A per flat (based on the surface area of a flat).

B. Antidote—of each candidate, 78 mg. was dissolved in 20 ml. of acetone with 1% Tween 20® (polyoxyethylene sorbitan monolaurate) so that 5 ml. when applied by preplant incorporation technique (PPI) is equal to 5 lb/A per flat.

The herbicide and antidotes were applied to the soil together as a tank mix employing pre-plant incorporation technique. To prepare the combined tank mix, 5 ml. of the VERNAM® were admixed, followed by incorporation into the soil from the flats during incorporation in a rotary mixer.

One row each of the following weeds and crop was seeded into the treated soil in the flats: Watergrass (*Echinochloa crusgalli*), foxtail (*Setaria viridis*), and soybeans (*Glycine max*).

The flats were placed on greenhouse benches where temperature were maintained between 70°–90° F. The soil was watered by sprinkling to assure good plant growth. Injury ratings were taken 2 and 4 weeks after the applications were made. Individual flats treated with the herbicide alone were included to provide a basis for determining the amount of injury reduction provided by the herbicide antidotes.

The following table includes results as percent protection for the crop according to the procedure discussed above. The percent protection is determined by a comparison with flats not treated with the candidate antidotes of this invention.

TABLE II

Application Method: Pre-plant Incorporation - PPI (Tank Mix)
Crop Species: Soybeans (*Glycine max*)
Weed Species: Foxtail (*Setaria viridis*)
Watergrass (*Echinochloa crusgalli*)

| COMPOUND NUMBER | PPI (6 lb/A) (Tank Mix) | | |
|---|---|---|---|
| | Soybeans | Watergrass | Foxtail |
| VERNAM 6 lb/A | 40* | 100* | 100* |
| 1** | 75 | 0 | 0 |
| 2 | 75 | 0 | 0 |
| 3 | 100 | 0 | 5 |
| 4 | 37.5 | 0 | 0 |
| 5 | 25 | 0 | 0 |
| 6 | 25 | 0 | 0 |
| 7 | 25 | 0 | 0 |
| 8 | 75 | 0 | 0 |
| 9 | 75 | 0 | 0 |
| 10 | 50 | 0 | 0 |
| 11 | 75 | 0 | 0 |
| 12 | 100 | 0 | 0 |
| 13 | 50 | 0 | 0 |
| 14 | 25 | 0 | 0 |
| 15 | 75 | 0 | 0 |
| 16 | 50 | 0 | 0 |
| 17 | 100 | 0 | 5 |
| 18 | 100 | 0 | 5 |
| 19 | 100 | 0 | 5 |
| 20 | 75 | 0 | 0 |
| 21 | 100 | 0 | 5 |
| 22 | 75 | 0 | 0 |
| 23$^a$ | 100 | 0 | 0 |
| 24$^a$ | 75 | 0 | 0 |
| 25$^a$ | 100 | 0 | 0 |
| 26$^a$ | 75 | 0 | 0 |
| 27$^a$ | 100 | 0 | 0 |
| 28$^a$ | 100 | 0 | 0 |
| 29$^1$ | 75 | 0 | 0 |
| 30$^a$ | 67.5 | 0 | 0 |

$^a$ = Pre-plant incorporation of VERNAM ® and antidote applied separately prior to incorporation.
* = % injury
** = % protection

Seed Treatment Test

Small flats were filled with Felton loamy sand soil. Soil incorporated herbicides were applied at this time. The soil from each flat was placed into a five-gallon cement mixer where the soil was mixed as the herbicides were applied using a pre-determined amount of a stock solution containing 780 mg. of approximately 75% active ingredient to 125 ml. of water. Five ml. of stock solution was applied to the soil in a volumetric pipet. Five ml. of stock solution contained an equivalence of herbicide which equals six (6) pounds per acre when applied to the soil in the flats. After the herbicide incorporation, the soil was placed back into the flats.

Flats of the herbicide-treated and untreated soil were then ready to be planted. A pint sample of soil was removed from each flat and placed next to each flat for later use in covering up the seeds. The soil was leveled and rows one-half inch deep were made for planting seeds. Alternating rows of treated and untreated crop seeds were sown. In each test, soybean (*Glycine max*) seeds were planted in each row. Rows were approximately 1½ inches apart in the flat. Seeds were treated by preparing a stock solution by dissolving 250 mg. of the antidote compound in 2.5 ml. of acetone, then using 0.5 ml. of the stock solution to treat 10 g. of soybean seed equivalent to 0.5% w/w. Antidote compounds can also be applied as liquid slurries and powders or dusts. In some cases, acetone is used to dissolve powdered or solid compounds so they could be more effectively applied to the seeds.

After the flats were seeded, they were covered with the one pint of soil which had been removed just prior to planting. Flats were placed on greenhouse benches where temperatures ranging from 70°-79° F. Flats were watered by sprinkling as needed to assure good plant growth. Percent control ratings were taken four weeks after the treatments were applied.

In each test, the herbicide was applied alone, in combination with the seed protectant, and the seed protectant was applied alone to check for phytotoxicity. The untreated adjacent row was employed to observe any beneficial lateral movement of the antidote compound through the soil. The degree of the effect was noted by comparison with the control.

In this seed treatment test with the herbicide S-n-propyl N,N-di-n-propyl thiocarbamate, Compound No. 17 exhibited 50% protection to the treated soybean seeds. That is, the injury was reduced by at least 50% to the emerging soybean plants grown from seed treated with Compound No. 17, compared to untreated seed grown in soil containing the thiocarbamate herbicide.

Evaluation Procedure and Method

Flats to be used for growing the crops and weed species were filled with loamy sand soil. Various methods of application were employed, such as pre-plant incorporation of (1) the herbicide and antidote separately, and (2) as a tank mix with the herbicide and antidote together. The application was by incorporation, whereinafter the seeds were planted in soil treated with an effective herbicidal composition of thiocarbamate herbicide and antidote; application by an in-furrow treatment of the seeds and surrounding soil in which the herbicide had been applied previously to the soil; and treatment of the crop seeds with an antidote candidate prior to planting in herbicide treated soil.

Stock solutions of other representative thiocarbamate herbicides and antidote candidates were prepared as follows:

Herbicides

C. S-ethyl di-n-propyl thiocarbamate-EPTC-EPTAM® 6E - 260 mg. dissolved in 200 ml. water such that 4 ml. applied to the soil from a planting flat is equivalent to 1 lb/A applied in 80 gal. of water per acre and 3 ml. is equivalent to 0.75 lb/A.

D. S-isopropyl 1-(5-ethyl-2-methyl-piperidine) carbothioate (R-12001), 390 mg. dissolved in 200 ml. of acetone with 1% Tween 20®, of 975 mg. in 250 ml. of acetone, such that 5 ml. of solution applied to a planting flat is equivalent to 2 lb/A pre-plant incorporated and 6 ml. is equivalent to 6 lb/A respectively.

E. S-ethyl di-isobutyl thiocarbamate-SUTAN® 6E or S-ethyl cyclohexyl ethyl thiocarbamate-RONEET® 6E - 520 mg. dissolved in 200 ml. water such that 4 ml. applied to the soil from a planting flat is equivalent to 2 lb/A, applied in 80 gal. of water per acre. For 6 lb/A or 12 lb/A, 1300 mg. or 26 mg. was dissolved in 250 ml. water, such that 6 ml. was equivalent to the desired amount, respectively.

F. 2,3,3-trichloroallyl N,N-diisopropyl thiocarbamate-AVADEX BW® 4E - 1219 mg. dissolved in 300 ml. distilled water, such that 6 ml. is equivalent to 3 lb/A when applied to the soil from a planting flat pre-plant incorporated.

G. S-ethyl hexahydro-1H-azepine-1-carbothioate-ORDRAM® 8E - 857 mg. dissolved in 250 ml. water such that 5 ml. is equivalent to 4 lb/A and 2.5 ml. is equivalent to 2 lb/A when applied to the soil from a planting flat preplant incorporated.

Antidotes

H. For each candidate compound employed, 250 mg. active ingredient was dissolved in 2.5 ml. acetone, with 1% Tween 20® (polyoxyethylene sorbitan monolaurate) such that 0.5 ml. of solution per 10 gm. of seeds is equal to ½% w/w. For seed treatment of ¼%, 0.25 ml. was diluted with 0.25 ml. of acetone, such that 0.5 ml. of solution for 10 gm. of seeds is equal to ¼% w/w. This solution was used for the seed treatment procedure in varying amounts and dilutions for example for 0.10%, 0.1 ml. is diluted with 0.4 ml. of acetone.

I. For each candidate compound employed in the "in-furrow" method of application, 95 mg. of active ingredient was dissolved in 15 ml. of acetone with 1% Tween 20® such that 1.5 ml. applied to the seed and soil in the furrow, in one-half of the flat was equivalent to 5 lb/A. When 1.0 lb/A is desired 0.3 ml. is diluted with 1.2 ml. of acetone.

J. For each candidate compound employed in the "tank mix" pre-plant incorporation test, 39 mg. of active ingredient was dissolved in 10 ml. of acetone with 1% Tween 20®, such that 5 ml. when applied to the soil of a flat was equivalent to 5 lb/A.

In-furrow application of the antidote employed the above stock solutions. As a preparatory step, a one pint sample of soil was removed from each flat to be retained and used later to cover the seeds after treatment with the stock solutions. The soil was leveled before planting. The herbicide stock solution was applied respectively to separate flats and pre-plant incorporated in the soil from the planting flat at the equivalent rate of 1 lb/A active ingredient of the indicated rate.

Rows ¼-inch deep were made lengthwise in each treated flat, preparatory to seeding. After seeding, the flats were sectioned into two equal portions using a wooden barrier and 1½ ml. of additive stock solution I was atomized directly onto the exposed seed and soil in the open furrow in one-half of the flat. The untreated section of the flat served as an herbicide check and also made it possible to observe any lateral movement of the antidote through the soil. The seeds were covered with the one pint sample of untreated soil which had been removed earlier.

For tank mixes to be applied as a pre-plant incorporated application, the following solutions and procedure were employed. Five milliliters (5 ml.) of herbicide stock solutions A or C were each mixed with five milliliters (5 ml.) of antidote candidate stock solution J such that the equivalent of 1 lb/A and 5 lbs/A of herbicide and antidote, respectively, were applied and incorporated into the soil of each flat. For pre-plant incorporation, the mixed stock solutions were injected into the soil during incorporation in a 5-gallon rotary mixer. Other stock solutions were employed at indicated rates in the tank mix procedure.

For seed treatment, 10 grams of seed in a suitable container was shaken with 0.5 ml. of antidote stock solution H, or other stock solution as indicated, such that the seed treatment was equivalent to 0.5% w/w, 0.25% w/w, 0.125% w/w or 0.1% w/w. Shaking was continued until the seeds were uniformly covered. The antidote compounds may be applied as liquid slurries and powder or dust treatments. The treated seeds were planted in soil in which herbicide stock solution had been pre-plant incorporated into the soil at a rate equivalent to 1 lb/A active ingredient.

All flats were placed on greenhouse benches where temperatures were maintained between 70°–90° F. The soil was watered by sprinkling to assure good plant growth. Injury ratings were taken 2 and 4 weeks after the applications were made. Individual control flats treated with the herbicide alone were included to provide a basis for determining the amount of injury reduction provided by the herbicide antidotes. The results of these tests are tabulated in Table III.

TABLE III

ANTIDOTE ACTIVITY

Application Method: Seed Treatment - ST
In-Furrow - IF
Pre-Plant Incorporation - PPI (Tank Mix)

Crop Species: Barley - BA [*Hordeum vulgare* (L.)]
Corn - CN [*Zea maize*]
Cotton - CT [*Gossypium hirsutum*]
Crop Species: Grain Sorghum - GS [*Sorghum vulgare*]
Rice - R [*Oryza sativa*]
Soybeans - SB [*Glycine max*]
Wheat - WT [*Triticum aestivum*]
Weed Species: Watergrass - WG [*Echinochloa crusgalli*]
Green Foxtail - FT [*Setaria viridis*]
Wild Oats - WO [*Avena fatua* (L.)]
Shattercane - SC [*Sorghum bicolor*]

Result = Percent injury with antidote present/percent injury of herbicide alone.

| Compound Number | Herbicide | Method of Application | Rate | Crop | Result |
|---|---|---|---|---|---|
| 1 | ORDRAM | PPI | 6+5 | CN | 60/90 |
|  | RONEET | PPI | 6+5 | CN | 85/95 |
|  | RONEET | PPI | 2+5 | GS | 40/50 |
|  | ORDRAM | PPI | 4+5 | SB | 70/80 |
|  | RONEET | PPI | 2+5 | SB | 60/70 |
|  | VERNAM | PPI | 6+5 | SB | 10/40 |
|  |  | IF | 6+5 | SB | 20/40 |
| 3 | ORDRAM | ST | 4+.125 | BA | 10/30 |
|  | RONEET | ST | 2+.10 | BA | 50/80 |
|  | R-12001 | PPI | 2+1 | BA | 30/60 |
|  |  | ST | 2+.25 | BA | 30/90 |
|  | VERNAM | ST | 1+.10 | BA | 40/60 |
|  | ORDRAM | PPI | 6+5 | CN | 50/90 |
|  | RONEET | PPI | 6+5 | CN | 30/95 |
|  |  | PPI | 6+0.5 | CN | 30/50 |
|  | VERNAM | PPI | 6+5 | CN | 60/75 |
|  | EPTAM | PPI | 0.75+5 | GS | 60/100 |
|  | ORDRAM | PPI | 2+5 | GS | 45/82 |
|  |  | ST | 2+.125 | GS | 55/75 |
|  | RONEET | PPI | 3+5 | GS | 40/75 |
|  |  | ST | 3+.125 | GS | 50/70 |
|  | R-12001 | PPI | 2+5 | GS | 58/92 |
|  |  | ST | 2+.125 | GS | 45/85 |
|  | SUTAN | PPI | 2+5 | GS | 50/95 |
|  |  | ST | 2+.125 | GS | 70/95 |
|  | VERNAM | ST | 1+.125 | GS | 65/95 |
|  | EPTAM | PPI | 5+1 | SB | 30/65 |
|  | ORDRAM | PPI | 4+1 | SB | 40/80 |
|  | RONEET | PPI | 2+5 | SB | 10/70 |
|  | SUTAN | PPI | 5+1 | SB | 45/65 |
|  | VERNAM | IF | 6+1 | SB | 0/40 |
|  |  | ST | 6+.062 | SB | 10/45 |
|  | ORDRAM | ST | 4+.125 | WT | 10/20 |
|  | RONEET | IF | 2+1 | WT | 75/90 |
|  | R-12001 | PPI | 2+1 | WT | 60/95 |

TABLE III-continued
ANTIDOTE ACTIVITY

|    |          |     |          |     |        |
|----|----------|-----|----------|-----|--------|
|    | R-12001  | ST  | 2+.062   | WT  | 40/70  |
|    | VERNAM   | IF  | 1+5      | WT  | 60/90  |
| 4  | ORDRAM   | PPI | 6+5      | CN  | 80/90  |
|    | RONEET   | PPI | 6+5      | CN  | 75/95  |
|    | RONEET   | PPI | 2+5      | SB  | 60/70  |
|    | VERNAM   | PPI | 6+5      |     | 25/40  |
| 5  | ORDRAM   | PPI | 6+5      | CN  | 80/90  |
|    | RONEET   | PPI | 6+5      | CN  | 80/95  |
|    | RONEET   | PPI | 2+5      | GS  | 40/50  |
| 6  | ORDRAM   | PPI | 6+5      | CN  | 80/90  |
|    | RONEET   | PPI | 6+5      | CN  | 80/95  |
|    | RONEET   | PPI | 2+5      | GS  | 40/50  |
|    | ORDRAM   | PPI | 4+5      | SB  | 50/80  |
| 7  | ORDRAM   | PPI | 6+5      | CN  | 70/90  |
|    | RONEET   | PPI | 6+5      |     | 70/95  |
|    | ORDRAM   | PPI | 4+5      | SB  | 70/80  |
| 8  | ORDRAM   | PPI | 6+5      | CN  | 80/90  |
|    | RONEET   | PPI | 6+5      | CN  | 80/95  |
|    | VERNAM   | IF  | 5+5      | CT  | 30/60  |
|    | RONEET   | PPI | 3+5      | GS  | 50/75  |
|    | VERNAM   | IF  | 6+5      | SB  | 20/40  |
| 9  | ORDRAM   | PPI | 6+5      | CN  | 70/90  |
|    | RONEET   | PPI | 6+5      | CN  | 70/95  |
|    | VERNAM   | IF  | 5+5      | CN  | 50/75  |
|    | VERNAM   | IF  | 1+5      | R   | 40/60  |
|    | VERNAM   | IF  | 1+5      | WT  | 60/87  |
| 10 | ORDRAM   | PPI | 6+5      | CN  | 80/90  |
|    | RONEET   | PPI | 6+5      | CN  | 75/95  |
|    | VERNAM   | IF  | 5+5      | CT  | 70/80  |
|    | ORDRAM   | PPI | 2+5      | GS  | 50/85  |
|    | RONEET   | PPI | 2+5      | GS  | 40/50  |
| 11 | ORDRAM   | PPI | 6+5      | CN  | 70/90  |
|    | RONEET   | PPI | 6+5      | CN  | 75/95  |
|    | VERNAM   | IF  | 6+5      | CN  | 0/70   |
|    | ORDRAM   | PPI | 2+5      | GS  | 75/85  |
|    | RONEET   | PPI | 2+5      | SB  | 50/70  |
|    | VERNAM   | IF  | 6+1      | SB  | 20/40  |
| 12 | ORDRAM   | PPI | 6+5      | CN  | 70/90  |
|    | RONEET   | PPI | 6+5      | CN  | 75/95  |
|    | ORDRAM   | PPI | 2+5      | GS  | 62/82  |
|    | RONEET   | PPI | 3+5      | GS  | 50/75  |
|    | R-12001  | PPI | 2+5      | GS  | 50/90  |
|    | VERNAM   | IF  | 1+5      | GS  | 50/100 |
|    | ORDRAM   | PPI | 4+5      | SB  | 20/80  |
|    | RONEET   | PPI | 2+5      | SB  | 40/70  |
|    | VERNAM   | IF  | 6+1      | SB  | 10/40  |
| 13 | RONEET   | PPI | 6+5      | CN  | 75/95  |
|    | VERNAM   | IF  | 5+5      | CT  | 60/80  |
|    | ORDRAM   | PPI | 4+5      | SB  | 70/80  |
|    | RONEET   | PPI | 2+5      | SB  | 60/70  |
| 14 | VERNAM   | IF  | 5+5      | BA  | 50/82  |
|    | VERNAM   | IF  | 5+5      | CN  | 50/70  |
|    | VERNAM   | IF  | 1+5      | WT  | 60/75  |
| 15 | ORDRAM   | PPI | 6+5      | CN  | 75/90  |
|    | VERNAM   | IF  | 5+5      | CN  | 40/50  |
|    | ORDRAM   | PPI | 2+5      | GS  | 70/85  |
|    | VERNAM   | IF  | 1+5      | GS  | 60/100 |
|    | EPTAM    | PPI | 5+5      | SB  | 35/65  |
|    | ORDRAM   | PPI | 4+5      | SB  | 50/80  |
|    | RONEET   | PPI | 2+5      | SB  | 50/70  |
|    | SUTAN    | PPI | 5+5      | SB  | 30/65  |
|    | VERNAM   | IF  | 6+1      | SB  | 20/50  |
| 16 | ORDRAM   | PPI | 6+5      | CN  | 80/90  |
|    | ORDRAM   | PPI | 2+5      | GS  | 60/85  |
|    | RONEET   | PPI | 2+5      | GS  | 40/50  |
|    | VERNAM   | IF  | 1+5      | GS  | 60/100 |
|    | ORDRAM   | PPI | 4+5      | SB  | 60/80  |
| 17 | ORDRAM   | ST  | 4+0.5    | BA  | 10/30  |
|    | RONEET   | ST  | 2+0.25   | BA  | 10/80  |
|    | R-12001  | PPI | 2+5      | BA  | 40/60  |
|    | R-12001  | ST  | 3+0.25   | BA  | 25/90  |
|    | SUTAN    | ST  | 2+0.25   | BA  | 0/75   |
|    | VERNAM   | IF  | 1+5      | BA  | 30/100 |
|    | ORDRAM   | PPI | 2+5      | GS  | 10/82  |
|    | ORDRAM   | ST  | 2+0.25   | GS  | 40/75  |
|    | RONEET   | PPI | 3+5      | GS  | 50/75  |
|    | RONEET   | ST  | 2+.25    | GS  | 10/70  |
|    | R-12001  | PPI | 2+5      | GS  | 68/92  |
|    | R-12001  | ST  | 2+0.25   | GS  | 25/85  |
|    | SUTAN    | ST  | 2+0.25   | GS  | 10/95  |
|    | VERNAM   | IF  | 1+5      | GS  | 40/100 |
|    | VERNAM   | ST  | 1+0.25   | GS  | 30/95  |
|    | EPTAM    | PPI | 5+5      | SB  | 40/57  |
|    | EPTAM    | ST  | 5+0.5    | SB  | 0/50   |
|    | SUTAN    | PPI | 5+5      | SB  | 30/65  |
|    | VERNAM   | IF  | 6+5      | SB  | 10/50  |
|    | ORDRAM   | ST  | 6+0.125  | WT  | 10/30  |
|    | R-12001  | PPI | 2+5      | WT  | 80/95  |
| 18 | ORDRAM   | ST  | 4+0.125  | BA  | 10/30  |
|    | RONEET   | ST  | 2+0.10   | BA  | 20/80  |
|    | R-12001  | PPI | 2+5      | BA  | 10/60  |
|    | R-12001  | ST  | 3+0.10   | BA  | 30/90  |
|    | SUTAN    | ST  | 2-0.10   | BA  | 0/75   |
|    | VERNAM   | IF  | 1+5      | BA  | 30/95  |
|    | VERNAM   | PPI | 1+5      | BA  | 40/95  |
|    | VERNAM   | ST  | 1+0.10   | BA  | 10/60  |
|    | ORDRAM   | PPI | 6+5      | CN  | 30/90  |
|    | RONEET   | PPI | 6+5      | CN  | 70/95  |
|    | R-12001  | PPI | 6+0.5    | CN  | 20/50  |
|    | VERNAM   | PPI | 6+5      | CN  | 50/75  |
|    | VERNAM   | IF  | 5+5      | CN  | 40/90  |
|    | EPTAM    | PPI | .75+5    | GS  | 50/100 |
|    | ORDRAM   | PPI | 2+5      | GS  | 30/82  |
|    | ORDRAM   | ST  | 2+0.125  | GS  | 50/75  |
|    | RONEET   | PPI | 2+5      | GS  | 20/75  |
|    | RONEET   | ST  | 2+0.125  | GS  | 20/70  |
|    | R-12001  | ST  | 2+0.125  | GS  | 50/85  |
|    | SUTAN    | PPI | 2+5      | GS  | 75/95  |
|    | SUTAN    | ST  | 2+0.125  | GS  | 60/95  |
|    | VERNAM   | PPI | 1+5      | GS  | 60/100 |
|    | VERNAM   | IF  | 1+5      | GS  | 40/100 |
|    |          | ST  | 1+0.125  | GS  | 60/95  |
|    | R-12001  | PPI | 2+5      | R   | 60/70  |
|    | VERNAM   | IF  | 1+5      | R   | 80/100 |
|    | EPTAM    | PPI | 5+5      | SB  | 20/65  |
|    | ORDRAM   | PPI | 4+5      | SB  | 40/80  |
|    | RONEET   | PPI | 2+5      | SB  | 30/70  |
|    | SUTAN    | PPI | 5+5      | SB  | 20/65  |
|    | VERNAM   | IF  | 6+1      | SB  | 13/50  |
|    |          | ST  | 6+0.125  | SB  | 15/25  |
|    | ORDRAM   | ST  | 4+0.125  | WT  | 5/30   |
|    | RONEET   | ST  | 1+0.25   | WT  | 70/95  |
|    | R-12001  | PPI | 2+5      | WT  | 75/95  |
|    |          | ST  | 2+0.63   | WT  | 40/70  |
|    | VERNAM   | IF  | 1+5      | WT  | 70/100 |
| 19 | R-12001  | PPI | 2+5      | BA  | 30/60  |
|    | VERNAM   | PPI | 1+5      | BA  | 40/95  |
|    | VERNAM   | IF  | 1+5      | BA  | 20/96  |
|    | ORDRAM   | PPI | 6+5      | CN  | 60/90  |
|    | RONEET   | PPI | 6+5      | CN  | 50/95  |
|    | VERNAM   | IF  | 5+5      | CN  | 50/90  |
|    | EPTAM    | PPI | 0.75+5   | GS  | 60/100 |
|    | ORDRAM   | PPI | 2+5      | GS  | 52/82  |
|    | RONEET   | PPI | 2+5      | GS  | 20/75  |
|    | R-12001  | PPI | 2+5      | GS  | 62/92  |
|    | SUTAN    | PPI | 2+5      | CS  | 70/95  |
|    | VERNAM   | PPI | 1+5      | GS  | 60/100 |
|    | VERNAM   | IF  | 1+5      | GS  | 50/100 |
|    | R-12001  | PPI | 2+5      | R   | 50/70  |
|    | VERNAM   | IF  | 1+5      | R   | 80/100 |
|    | RONEET   | PPI | 2+5      | SB  | 40/70  |
|    | VERNAM   | IF  | 6+1      | SB  | 10/40  |
|    | R-12001  | PPI | 2+1      | WT  | 50/95  |
|    | VERNAM   | IF  | 1+5      | WT  | 80/100 |
| 20 | VERNAM   | IF  | 1+5      | BA  | 50/95  |
|    | ORDRAM   | PPI | 6+5      | CN  | 70/90  |
|    | RONEET   | PPI | 6+5      | CN  | 70/95  |
|    | VERNAM   | IF  | 5+5      | CN  | 70/90  |
|    | VERNAM   | IF  | 5+5      | CT  | 60/80  |
|    | VERNAM   | IF  | 1+5      | R   | 85/100 |
|    | VERNAM   | IF  | 6+1      | SB  | 20/40  |
| 21 | R-12001  | PPI | 2+5      | BA  | 30/60  |
|    | VERNAM   | PPI | 1+5      | BA  | 60/95  |
|    | VERNAM   | IP  | 1+5      | BA  | 30/95  |
|    | ORDRAM   | PPI | 6+5      | CN  | 60/90  |
|    | RONEET   | PPI | 6+5      | CN  | 70/95  |
|    | VERNAM   | IF  | 5+5      | CN  | 60/90  |
|    | EPTAM    | PPI | 0.75+5   | GS  | 40/100 |
|    | ORDRAM   | PPI | 2+5      | GS  | 25/82  |
|    | RONEET   | PPI | 2+5      | GS  | 40/75  |
|    | R-12001  | PPI | 2+5      | GS  | 45/92  |
|    | SUTAN    | PPI | 2+5      | BA  | 30/95  |

TABLE III-continued
ANTIDOTE ACTIVITY

|    |         |     |          |    |        |
|----|---------|-----|----------|-----|--------|
|    | VERNAM  | PPI | 1+5      | GS | 60/100 |
|    | VERNAM  | IF  | 1+5      | GS | 40/100 |
|    | R-12001 | PPI | 2+5      | GS | 40/70  |
|    | RONEET  | PPI | 2+5      | SB | 50/70  |
|    | VERNAM  | IF  | 6+1      | SB | 25/50  |
|    | R-12001 | PPI | 2+5      | WT | 50/95  |
|    | VERNAM  | IF  | 1+5      | WT | 80/100 |
| 22 | ORDRAM  | PPI | 6+5      | CN | 60/90  |
|    | RONEET  | PPI | 6+5      | CN | 85/95  |
|    | ORDRAM  | PPI | 4+5      | SB | 70/80  |
|    | RONEET  | PPI | 2+5      | SB | 60/70  |
|    | VERNAM  | IF  | 6+1      | SB | 30/40  |
| 23 | VERNAM  | IF  | 1+5      | BA | 20/90  |
|    | VERNAM  | IF  | 5+5      | CN | 20/90  |
|    | EPTAM   | PPI | 0.75+5   | GS | 70/100 |
|    | ORDRAM  | PPI | 2+5      | GS | 60/80  |
|    | RONEET  | PPI | 3+5      | GS | 50/75  |
|    | RONEET  | IF  | 3+5      | GS | 30/75  |
|    | R-12001 | PPI | 2+5      | GS | 50/90  |
| 24 | VERNAM  | IF  | 1+5      | BA | 10/90  |
|    | VERNAM  | IF  | 5+5      | CN | 50/90  |
|    | EPTAM   | PPI | 0.75+5   | GS | 40/100 |
|    | ORDRAM  | PPI | 2+5      | GS | 40/80  |
|    | RONEET  | PPI | 3+5      | GS | 20/75  |
|    | RONEET  | IF  | 2+5      | GS | 30/65  |
|    | R-12001 | PPI | 2+5      | GS | 30/90  |
|    | SUTAN   | PPI | 2+5      | GS | 40/95  |
|    | VERNAM  | IF  | 1+5      | GS | 20/96  |
| 25 | VERNAM  | IF  | 1+5.     | BA | 20/70  |
|    | VERNAM  | IF  | 5+5      | CN | 20/90  |
|    | RONEET  | IF  | 2+5      | GS | 30/65  |
|    | VERNAM  | IF  | 1+5      | GS | 30/96  |
|    | VERNAM  | IF  | 1+5      | R  | 50/100 |
| 26 | VERNAM  | IF  | 5+5      | CN | 60/90  |
|    | VERNAM  | IF  | 1+5      | GS | 60/96  |
| 27 | ORDRAM  | ST  | 4+0.125  | BA | 0/30   |
|    | RONEET  | ST  | 2+0.25   | BA | 10/80  |
|    | R-12001 | PPI | 2+5      | BA | 10/60  |
|    | R-12001 | ST  | 3+0.125  | BA | 0/70   |
|    | SUTAN   | ST  | 2+0.25   | BA | 0/75   |
|    | VERNAM  | IF  | 1+5      | BA | 10/70  |
|    | VERNAM  | ST  | 1+0.10   | BA | 20/60  |
|    | VERNAM  | IF  | 5+5      | CN | 40/90  |
|    | EPTAM   | PPI | 0.75+5   | CT | 50/100 |
|    | ORDRAM  | PPI | 2+5      | CT | 50/80  |
|    | ORDRAM  | ST  | 2+0.125  | CT | 40/75  |
|    | RONEET  | PPI | 3+5      | CT | 30/75  |
|    | RONEET  | IF  | 3+1      | CT | 40/65  |
|    | RONEET  | ST  | 3+0.125  | CT | 20/70  |
|    | R-12001 | PPI | 2+5      | CT | 50/92  |
|    | R-12001 | ST  | 2+0.125  | CT | 30/85  |
|    | SUTAN   | ST  | 2+0.125  | CT | 30/95  |
|    | EPTAM   | PPI | 0.75+5   | GS | 50/100 |
|    | ORDRAM  | PPI | 2+5      | GS | 50/80  |
|    | ORDRAM  | ST  | 2+0.125  | GS | 40/75  |
|    | RONEET  | PPI | 3+5      | GS | 30/75  |
|    |         | IF  | 3+1      | GS | 40/65  |
|    |         | ST  | 3+0.125  | GS | 20/70  |
|    | R-12001 | ST  | 2+0.125  | GS | 30/85  |
|    | SUTAN   | ST  | 2+0.125  | GS | 30/95  |
|    | VERNAM  | IF  | 1+5      | GS | 30/96  |
|    | ORDRAM  | ST  | 6+0.125  | WT | 10/30  |
|    | R-12001 | ST  | 2+0.062  | WT | 40/70  |
| 28 | VERNAM  | IF  | 1+5      | BA | 20/70  |
|    | VERNAM  | IF  | 5+5      | CN | 50/90  |
|    | ORDRAM  | ST  | 2+0.125  | GS | 45/75  |
|    | RONEET  | IF  | 2+5      | GS | 40/65  |
|    | RONEET  | ST  | 3+0.125  | GS | 30/70  |
|    | R-12001 | PPI | 2+5      | GS | 50/95  |
|    | R-12001 | ST  | 2+0.125  | GS | 30/85  |
|    | SUTAN   | ST  | 2+0.125  | GS | 40/95  |
|    | VERNAM  | IF  | 1+5      | GS | 20/96  |
|    | VERNAM  | ST  | 1+0.125  | GS | 40/95  |
|    | ORDRAM  | ST  | 6+0.125  | WT | 0/40   |
|    | R-12001 | PPI | 2+5      | WT | 50/95  |
|    | R-12001 | ST  | 2+.125   | WT | 30/70  |
| 29 | ORDRAM  | ST  | 4+0.125  | BA | 10/30  |
|    | R-12001 | PPI | 2+1      | BA | 40/60  |
|    | VERNAM  | ST  | 1+0.50   | BA | 50/95  |
|    | EPTAM   | PPI | 5+5      | CN | 20/85  |
|    | R-12001 | PPI | 5+0.5    | CN | 20/50  |
|    | EPTAM   | PPI | 0.75+5   | GS | 40/100 |
|    | ORDRAM  | PPI | 2+5      | GS | 30/80  |
|    | ORDRAM  | ST  | 2+0.125  | GS | 40/75  |
|    | RONEET  | PPI | 3+5      | GS | 30/75  |
|    | RONEET  | IF  | 3+2      | GS | 40/65  |
|    | RONEET  | ST  | 3+0.125  | GS | 20/70  |
|    | SUTAN   | PPI | 2+5      | GS | 30/95  |
| 30 | VERNAM  | IF  | 1+5      | GS | 40/100 |
| 31 | VERNAM  | PPI | 6+5      | SB | 15/40  |
|    | EPTAM   | PPI | 5+5      | CN | 30/85  |
|    | VERNAM  | IF  | 5+5      | SB | 10/40  |
| 32 | VERNAM  | IF  | 1+5      | BA | 60/70  |
|    | VERNAM  | IF  | 1+5      | CT | 40/60  |
|    | VERNAM  | IF  | 1+5      | GS | 70/100 |
|    | VERNAM  | IF  | 1+5      | SB | 0/42   |
| 33 | VERNAM  | IF  | 1+5      | BA | 60/70  |
|    | VERNAM  | IF  | 1+5      | GS | 50/100 |
|    | VERNAM  | IF  | 1+5      | R  | 70/95  |
|    | VERNAM  | IF  | 1+5      | SB | 30/60  |
| 34 | VERNAM  | IF  | 1+5      | BA | 50/70  |
|    | VERNAM  | IF  | 1+5      | CN | 70/90  |
|    | VERNAM  | IF  | 1+5      | GS | 60/100 |
|    | VERNAM  | IF  | 6+1      | SB | 10/42  |
| 35 | VERNAM  | IF  | 1+5      | BA | 60/70  |
|    | VERNAM  | IF  | 1+5      | CT | 40/60  |
|    | VERNAM  | IF  | 1+5      | GS | 50/100 |
|    | VERNAM  | IF  | 6+5      | SB | 20/42  |
| 36 | VERNAM  | IF  | 1+5      | BA | 30/60  |
|    | VERNAM  | IF  | 1+5      | CN | 50/95  |
|    | VERNAM  | IF  | 1+5      | GS | 50/100 |
| 37 | VERNAM  | IF  | 1+5      | BA | 20/60  |
|    | VERNAM  | IF  | 6+5      | CN | 60/95  |
|    | VERNAM  | IF  | 1+5      | CT | 20/50  |
|    | VERNAM  | IF  | 1+5      | GS | 40/100 |
|    | VERNAM  | IF  | 1+5      | WT | 60/90  |
| 38 | VERNAM  | IF  | 1+5      | BA | 20/60  |
|    | VERNAM  | IF  | 6+5      | CN | 10/95  |
|    | VERNAM  | IF  | 6+5      | SB | 20/50  |
| 39 | RONEET  | PPI | 6+5      | CN | 75/95  |
| 40 | VERNAM  | IF  | 1+5      | BA | 60/100 |
|    | ORDRAM  | PPI | 6+5      | CN | 70/90  |
|    | VERNAM  | IF  | 1+5      | GS | 60/100 |
|    | VERNAM  | PPI | 6+5      | SB | 10/40  |
| 41 | VERNAM  | IF  | 1+5      | BA | 40/50  |
|    | ORDRAM  | PPI | 2+5      | GS | 60/80  |
| 42 | VERNAM  | IF  | 1+5      | BA | 30/50  |
|    | RONEET  | PPI | 2+5      | GS | 40/75  |
|    | VERNAM  | PPI |          | SB | 40/60  |
| 43 | ORDRAM  | PPI | 6+5      | CN | 70/90  |
|    | RONEET  | PPI | 2+5      | GS | 40/50  |
|    | ORDRAM  | PPI | 4+5      | SB | 50/80  |
|    | VERNAM  | IF  | 1+5      | WT | 60/90  |
| 44 | VERNAM  | IF  | 6+5      | CN | 50/70  |
|    | VERNAM  | IF  | 1+5      | CT | 40/70  |
|    | RONEET  | PPI | 3+5      | GS | 60/75  |
| 45 | VERNAM  | IF  | 1+5      | R  | 40/95  |
|    | VERNAM  | PPI | 4+5      | SB | 40/50  |
| 46 | VERNAM  | IF  | 1+5      | BA | 30/50  |
|    | RONEET  | PPI | 3+5      | GS | 50/75  |
|    | VERNAM  | IF  | 1+5      | R  | 30/95  |
| 47 | VERNAM  | PPI | 6+1      | SB | 10/40  |
|    | VERNAM  | IF  | 6+5      | SB | 60/80  |
|    | VERNAM  | IF  | 1+5      | WT | 50/75  |
| 48 | ORDRAM  | PPI | 2+5      | GS | 60/85  |
|    | VERNAM  | PPI | 6+5      | SB | 30/40  |
| 49 | VERNAM  | IF  | 5+5      | CN | 40/70  |
|    | RONEET  | PPI | 2+5      | SB | 50/70  |
|    | VERNAM  | PPI | 6+5      | SB | 30/40  |
| 50 | VERNAM  | IF  | 1+5      | BA | 60/90  |
|    | VERNAM  | IF  | 1+5      | R  | 50/90  |
|    | ORDRAM  | PPI | 4+5      | SB | 50/80  |
|    | VERNAM  | IF  | 6+1      | SB | 30/40  |
| 51 | VERNAM  | IF  | 1+5      | BA | 30/83  |
|    | EPTAM   | PPI | 0.75+5   | GS | 50/100 |
|    | ORDRAM  | ST  | 2+0.125  | GS | 50/75  |
|    | RONEET  | ST  | 3+0.125  | GS | 30/70  |
|    | VERNAM  | IF  | 1+5      | GS | 60/100 |
|    | VERNAM  | IF  | 6+0.5    | SB | 10/40  |
| 52 | EPTAM   | PPI | 0.75+5   | GS | 50/100 |
|    | RONEET  | PPI | 3+5      | GS | 20/75  |
|    | RONEET  | IF  | 3+1      | GS | 40/75  |

TABLE III-continued
ANTIDOTE ACTIVITY

| | | | | | |
|---|---|---|---|---|---|
| | SUTAN | PPI | 2+5 | GS | 40/95 |
| | VERNAM | IF | 1+5 | GS | 40/100 |
| | VERNAM | PPI | 6+5 | SB | 10/50 |
| | | IF | 6+5 | SB | 10/30 |
| 53 | ORDRAM | PPI | 6+5 | CN | 50/90 |
| | ORDRAM | PPI | 2+5 | GS | 60/85 |
| | VERNAM | IF | 1+5 | R | 50/95 |
| 54 | VERNAM | IF | 1+5 | BA | 10/60 |
| | VERNAM | IF | 6+5 | CN | 40/70 |
| | EPTAM | PPI | 0.75+5 | GS | 30/100 |
| | ORDRAM | PPI | 2+5 | GS | 40/80 |
| | RONEET | PPI | 3+5 | GS | 20/75 |
| | RONEET | IF | 3+5 | GS | 10/75 |
| | R-12001 | PPI | 2+5 | GS | 20/90 |
| | SUTAN | PPI | 2+5 | GS | 30/95 |
| | VERNAM | IF | 1+5 | GS | 30/100 |
| | VERNAM | PPI | 6+5 | SB | 0/50 |
| | VERNAM | IF | 1+5 | WT | 60/90 |
| 55 | ORDRAM | PPI | 6+5 | CN | 70/90 |
| | VERNAM | IF | 6+5 | CN | 70/90 |
| | VERNAM | IF | 1+5 | GS | 75/100 |
| | VERNAM | PPI | 6+5 | SB | 10/40 |
| | VERNAM | IF | 6+1 | SB | 20/40 |
| | VERNAM | IF | 6+5 | SB | 20/40 |
| 56 | ORDRAM | PPI | 6+5 | CN | 70/90 |
| | RONEET | PPI | 2+5 | GS | 40/50 |
| | VERNAM | PPI | 6+5 | SB | 10/40 |
| | VERNAM | IF | 6+1 | SB | 20/40 |
| 57 | VERNAM | PPI | 6+0.5 | SB | 20/40 |
| | VERNAM | IF | 6+5 | SB | 40/60 |
| 58 | VERNAM | PPI | 6+1 | SB | 10/40 |
| | VERNAM | IF | 1+5 | WT | 50/78 |
| 59 | VERNAM | IF | 1+5 | GS | 70/100 |
| | VERNAM | PPI | 6+5 | SB | 30/50 |
| | VERNAM | IF | 6+5 | SB | 10/30 |
| 60 | VERNAM | IF | 1+5 | BA | 30/55 |
| | VERNAM | IF | 1+5 | GS | 60/85 |
| 61 | VERNAM | IF | 6+5 | CN | 80/90 |
| | VERNAM | IF | 1+5 | CT | 40/50 |
| 62 | VERNAM | IF | 1+5 | BA | 30/55 |
| | VERNAM | IF | 6+5 | CN | 70/90 |
| 63 | VERNAM | IF | 1+5 | BA | 20/55 |
| | VERNAM | IF | 6+5 | CN | 50/90 |
| | VERNAM | IF | 6+5 | SB | 30/55 |
| 64 | VERNAM | IF | 1+5 | CT | 40/60 |
| | VERNAM | IF | 1+5 | GS | 40/100 |
| 65 | VERNAM | IF | 1+5 | BA | 40/60 |
| | VERNAM | IF | 1+5 | CN | 30/95 |
| | VERNAM | IF | 1+5 | GS | 40/95 |
| | VERNAM | IF | 6+5 | SB | 0/60 |
| 66 | VERNAM | IF | 1+5 | BA | 30/55 |
| | VERNAM | IF | 6+5 | CN | 30/90 |
| | VERNAM | IF | 1+5 | GS | 40/85 |
| 67 | VERNAM | IF | 1+5 | BA | 40/55 |
| | VERNAM | IF | 6+5 | CN | 70/90 |
| | VERNAM | IF | 1+5 | GS | 60/85 |
| | VERNAM | IF | 1+5 | WT | 60/70 |
| 68 | VERNAM | IF | 1+5 | BA | 30/55 |
| | VERNAM | IF | 6+5 | CN | 30/90 |
| | VERNAM | IF | 1+5 | GS | 40/85 |
| | VERNAM | IF | 6+5 | SB | 30/55 |
| | VERNAM | IF | 1+5 | WT | 50/70 |
| 69 | VERNAM | IF | 1+5 | BA | 20/55 |
| | VERNAM | IF | 6+5 | CN | 30/90 |
| | VERNAM | IF | 1+5 | GS | 40/85 |
| 70 | VERNAM | IF | 1+5 | BA | 30/55 |
| | VERNAM | IF | 6+5 | CN | 40/90 |
| | VERNAM | IF | 1+5 | GS | 30/85 |
| | VERNAM | IF | 6+5 | SB | 30/55 |
| 71 | VERNAM | IF | 1+5 | BA | 40/50 |
| | VERNAM | IF | 5+5 | SB | 10/40 |
| 72 | VERNAM | IF | 1+5 | WT | 40/75 |
| 73 | VERNAM | IF | 6+5 | SB | 30/60 |
| 74 | VERNAM | IF | 1+5 | WT | 50/75 |
| 75 | VERNAM | IF | 1+5 | BA | 30/50 |
| | VERNAM | IF | 1+5 | WT | 40/75 |
| 76 | VERNAM | IF | 1+5 | CT | 55/70 |
| | VERNAM | IF | 1+5 | WT | 50/75 |
| 77 | VERNAM | IF | 1+5 | BA | 30/60 |
| | VERNAM | IF | 6+1 | SB | 10/40 |
| 78 | R-12001 | IF | 6+5 | CT | 50/65 |
| | VERNAM | IF | 1+5 | CT | 10/50 |

TABLE III-continued
ANTIDOTE ACTIVITY

| | | | | | |
|---|---|---|---|---|---|
| | VERNAM | IF | 6+5 | SB | 40/60 |
| 79 | VERNAM | IF | 6+5 | SB | 30/60 |
| 80 | VERNAM | IF | 1+5 | BA | 40/70 |
| | VERNAM | IF | 1+5 | CT | 40/60 |
| | VERNAM | IF | 1+5 | R | 60/95 |
| | VERNAM | IF | 6+5 | SB | 40/60 |
| 81 | VERNAM | IF | 1+5 | CT | 40/50 |
| 82 | VERNAM | IF | 1+5 | GS | 60/100 |
| | VERNAM | PPI | 6+0.5 | SB | 20/40 |
| 83 | VERNAM | IF | 6+5 | CN | 50/95 |
| | VERNAM | IF | 1+5 | CT | 30/50 |
| | VERNAM | IF | 1+5 | GS | 80/100 |
| | VERNAM | IF | 6+1 | SB | 10/50 |
| 84 | VERNAM | IF | 1+5 | GS | 70/95 |
| | VERNAM | IF | 6+1 | SB | 0/40 |
| 85 | RONEET | IF | 3+5 | GS | 30/75 |
| | VERNAM | IF | 1+5 | GS | 50/100 |
| | VERNAM | PPI | 6+5 | SB | 10/50 |
| 86 | VERNAM | IF | 1+5 | BA | 70/83 |
| | VERNAM | IF | 6+5 | CN | 60/90 |
| | VERNAM | IF | 1+5 | GS | 70/100 |
| | VERNAM | PPI | 6+1 | SB | 20/40 |
| 87 | VERNAM | IF | 6+5 | CN | 80/90 |
| | VERNAM | IF | 1+5 | GS | 60/100 |
| | VERNAM | IF | 6+5 | SB | 40/60 |
| 88 | VERNAM | IF | 6+5 | CN | 80/00 |
| | VERNAM | IF | 1+5 | GS | 80/100 |
| | VERNAM | IF | 6+1 | SB | 10/42 |
| 89 | VERNAM | IF | 1+5 | CT | 10/50 |
| | VERNAM | IF | 6+5 | SB | 30/60 |
| 90 | VERNAM | IF | 1+5 | BA | 30/55 |
| | VERNAM | IF | 6+1 | SB | 0/50 |
| | VERNAM | IF | 1+5 | WT | 60/85 |
| 91 | VERNAM | IF | 1+5 | CT | 20/50 |
| | VERNAM | IF | 6+5 | SB | 30/55 |
| 92 | VERNAM | IF | 1+5 | BA | 20/55 |
| | VERNAM | IF | 1+5 | CT | 30/50 |
| | VERNAM | IF | 6+5 | SB | 20/50 |
| 93 | VERNAM | IF | 1+5 | GS | 60/95 |
| | VERNAM | IF | 6+5 | SB | 40/60 |
| 94 | VERNAM | IF | 1+5 | GS | 80/100 |
| | VERNAM | IF | 6+5 | SB | 30/50 |
| | VERNAM | IF | 6+5 | WT | 70/85 |
| 95 | VERNAM | IF | 6+5 | CN | 80/90 |
| | VERNAM | IF | 1+5 | R | 20/70 |
| 96 | VERNAM | IF | 1+5 | BA | 40/70 |
| | VERNAM | IF | 1+5 | CT | 40/60 |
| | VERNAM | IF | 1+5 | R | 60/95 |
| | VERNAM | IF | 6+5 | SB | 30/60 |
| 97 | VERNAM | IF | 1+5 | BA | 40/55 |
| 98 | VERNAM | IF | 6+5 | SB | 30/55 |
| 99 | VERNAM | IF | 1+5 | BA | 30/55 |
| | VERNAM | IF | 1+5 | R | 20/70 |
| 100 | VERNAM | IF | 1+5 | BA | 30/55 |
| | VERNAM | IF | 1+5 | R | 60/70 |
| 101 | VERNAM | IF | 1+5 | BA | 40/55 |
| | VERNAM | IF | 6+5 | SB | 20/50 |
| | VERNAM | IF | 1+5 | WT | 60/85 |
| 102 | VERNAM | IF | 1+5 | BA | 30/55 |
| | VERNAM | IF | 1+5 | CT | 40/50 |
| | VERNAM | IF | 6+5 | SB | 0/50 |
| 103 | R-12001 | IF | 6+5 | CT | 50/65 |
| | VERNAM | IF | 1+5 | CT | 30/50 |
| | VERNAM | IF | 6+5 | SB | 0/60 |
| | VERNAM | IF | 1+5 | WT | 60/85 |
| 104 | VERNAM | IF | 1+5 | BA | 40/55 |
| | VERNAM | IF | 6+5 | SB | 30/60 |
| | VERNAM | IF | 1+5 | WT | 60/70 |
| 105 | VERNAM | IF | 1+5 | BA | 40/55 |
| | VERNAM | IF | 6+5 | SB | 0/60 |
| | VERNAM | IF | 1+5 | WT | 60/85 |
| 106 | VERNAM | IF | 1+5 | BA | 30/60 |
| | VERNAM | IF | 6+5 | CN | 70/95 |
| | VERNAM | IF | 6+5 | SB | 30/60 |
| 107 | VERNAM | IF | 6+5 | SB | 0/60 |
| | VERNAM | IF | 1+5 | WT | 60/85 |

In side-by-side tests with various weed species and crops, it was found that weed control was maintained while at the same time the crop species were protected or injury decreased, when compared to a check or control flat. The control flat contained no antidote compound candidate. The following table further exemplifies those results.

TABLE IV

| HERBICIDE | RATE | Percent Injury | | |
|---|---|---|---|---|
| | | GS | SC | WG |
| RONEET ® | 3 lb/A (PPI) | 50 | 50 | 100 |

| COMPOUND NUMBER | RATE (IF) | GS | SC | WG |
|---|---|---|---|---|
| 2 | 1 lb/A | 40 | 100 | 100 |
| 33 | 1 lb/A | 30 | 100 | 100 |
| 35 | 1 lb/A | 30 | 100 | 100 |
| 36 | 1 lb/A | 10 | 100 | 100 |
| 37 | 1 lb/A | 25 | 100 | 100 |
| 38 | 1 lb/A | 30 | 100 | 100 |
| 64 | 1 lb/A | 30 | 100 | 100 |
| 65 | 1 lb/A | 15 | 100 | 100 |
| 68 | 1 lb/A | 40 | 100 | 100 |
| 69 | 1 lb/A | 40 | 100 | 100 |
| 70 | 1 lb/A | 15 | 100 | 100 |
| 93 | 1 lb/A | 40 | 100 | 100 |
| 93 | 5 lb/A | 30 | 100 | 100 |
| 106 | 1 lb/A | 40 | 100 | 100 |

| HERBICIDE | RATE | Percent Injury | | | |
|---|---|---|---|---|---|
| | | RC | WT | WG | WO |
| ORDRAM ® | 8 lb/A (PPI) | 25 | 30 | 100 | 100 |

| COMPOUND NUMBER | RATE (IF) | RC | WT | WG | WO |
|---|---|---|---|---|---|
| 3 | 1 lb/A | 50 | 20 | 100 | 100 |
| | 5 lb/A | 0 | 60 | 0 | 0 |
| 17 | 1 lb/A | 50 | 10 | 100 | 100 |
| | 5 lb/A | 20 | 0 | 100 | 100 |
| 18 | 5 lb/A | 20 | 10 | 100 | 100 |
| 19 | 1 lb/A | 60 | 20 | 100 | 100 |
| | 5 lb/A | 0 | 60 | 100 | 100 |
| 25 | 1 lb/A | 40 | 10 | 100 | 100 |
| | 5 lb/A | 10 | 10 | 100 | 100 |
| 27 | 1 lb/A | 60 | 10 | 100 | 100 |
| | 5 lb/A | 10 | 60 | 100 | 100 |
| 29 | 5 lb/A | 20 | 10 | 100 | 100 |
| 47 | 5 lb/A | 20 | 20 | 100 | 100 |
| 51 | 5 lb/A | 40 | 20 | 100 | 100 |
| 94 | 5 lb/A | 40 | 10 | 100 | 100 |
| 96 | 5 lb/A | 60 | 10 | 100 | 100 |
| 32 | 1 lb/A | 40 | 20 | 100 | 100 |
| | 5 lb/A | 0 | 10 | 80 | 100 |
| 35 | 1 lb/A | 10 | 10 | 100 | 100 |
| 37 | 1 lb/A | 40 | 10 | 100 | 100 |
| 38 | 5 lb/A | 30 | 10 | 100 | 100 |

| HERBICIDE | RATE | Percent Injury | | |
|---|---|---|---|---|
| | | C | WG | FT |
| SUTAN ® | 12 lb/A | 50 | 100 | 100 |

| COMPOUND NUMBER | RATE (PPI TANK MIX | C | WG | FT |
|---|---|---|---|---|
| 3 | 5 lb/A | 20 | 100 | 100 |
| 18 | 5 lb/A | 40 | 100 | 100 |
| 19 | 5 lb/A | 40 | 100 | 100 |
| 21 | 5 lb/A | 40 | 100 | 100 |
| 23 | 5 lb/A | 40 | 100 | 100 |
| 24 | 5 lb/A | 30 | 100 | 100 |
| 29 | 5 lb/A | 20 | 100 | 100 |
| 51 | 5 lb/A | 20 | 100 | 100 |

The compounds and compositions of this invention were employed in effective herbicidal compositions comprising the antidote and a thiocarbamate herbicide as described hereinabove. The herbicidal compositions were tested in the above manner.

A preferred herbicidal composition comprises a thiocarbamate herbicide and an antidotally effective amount of an antidote compound therefor corresponding to the formula in

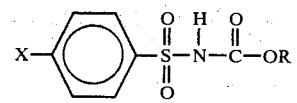

which X is hydrogen, methyl, methoxy, chloro or bromo; and R is alkyl having 1 to 4 carbon atoms, inclusive, haloalkyl having 2 to 6 carbon atoms, inclusive, wherein halo is chloro, bromo or fluoro from 1 to 6, inclusive, alkenyl having 3 to 6 carbon atoms, inclusive, chloroalkenyl having 3 to 6 carbon atoms, inclusive, or alkynyl having 3 to 6 carbon atoms, inclusive, dialkylamino, having 2 to 6 carbon atoms, inclusive, trifluoracetamidomethyl, 4-chlorophenylthiomethyl, phenyl, 3-phenylpropyn-2-yl, 3-pyridylmethyl and phosphonomethyl.

The compositions of the present invention for the protection of cultivated crop plants comprise the active herbicidal compound and an antidote therefor selected from the above-described compounds. The compositions of herbicide and antidote can be prepared by conventional methods through the thorough mixing and grinding of the active herbicide agents and the antidote with suitable carriers and/or other distribution media, possibly with the addition of dispersion agents or solvents.

The antidote compounds and compositions of the present invention can be used in any convenient form. A solvent or inert carrier is not necessary in view of low volume spray technology which permits the use of neat technical grade materials as sprays. Thus, the antidote compounds and composition with the thiocarbamate herbicide can be formulated into emulsifiable liquids, emulsifiable concentrates, liquid, wettable powder, powders, granular or any other convenient form. In its preferred form, a non-phytotoxic quantity of an herbicidal antidote compound is admixed with a selected herbicide and incorporated into the soil prior to or after planting the seed. It is to be understood, however, that the herbicide can be incorporated into the soil and thereafter the antidote compound can be incorporated into the soil. Moreover, the crop seed itself can be treated with a non-pytotoxic quantity of the compound and planted into the soil which has been treated with herbicide, or untreated with the herbicide and subsequently treated with the herbicide. The addition of the antidote compound does not affect the herbicidal activity of the herbicide. The alternative methods of application have been exemplified in the above examples.

The amount of antidote compound present can range between about 0.001 to about 30 parts by weight of antidote compound described herein per each part by weight of herbicide. The exact amount of antidote compound will usually be determined on economic ratios for the most effective amount usable. It is understood that a non-phytotoxic, but effective quantity of antidote compound will be employed in the herbicidal compositions and methods described herein.

After treatment with the antidote and herbicide there is obtain as a resultant thereof, soil which is novel in composition. Said soil is improved in its capability to grow crops and to offer weed control. Further said soil treated with herbicide and antidote has the particular utility for allowing seed of crops otherwise injured by the herbicide to be planted and grown. The herbicide has its utility in controlling undesirable vegetation; the antidote compound decrease the injury from the herbicide upon the crop species, and the soil treated with herbicide and antidote compound provides an improved media to grow the crop in the presence of an otherwise injurious herbicide.

In the utility of the present antidote compounds and improved herbicide system the thiocarbamate can be applied to the soil. Application of the herbicide to the soil can take place by preplant incorporation. In conjunction with the prior application of the herbicide employing the present invention crop seeds are planted. Seed planting is followed by application of the antidote as a preemergence surface application. This sequence of application of herbicide, seed planting and antidote is unusual and fully effective in decreasing injury to the plant crop, otherwise injured by the thiocarbamate.

Legume Evaluation Test

Various antidote compounds described herein have been found capable of decreasing injury to the class of crops known as legumes. By legumes is meant those plants that have a symbiotic relationship with nitrogen fixing organisms. For example, soybeans, varieties of *Phaeseolus vulgaris* (L.), peanuts, alfalfa, clover and the like.

The following test was performed to determine the efficacy as decreased injury of the legume crops by a representative thiocarbamate herbicide, EPTAM® (EPTC), S-ethyl di-n-propyl thiocarbamate with compounds described herinabove. Various edible bean and pea varieties were tested. The antidotes were applied at 1 and 2 lb/A preplant incorporated, tank mixed with EPTC at 6 lb/A preplant incorporated.

Stock Solutions:

Antidote: For each candidate compound employed 39 mg. dissolved in 25 ml. acetone; 2.5 ml. equivalent to 1 lb/A preplant incorporated.

Herbicide: EPTAM® 6E: 1560 mg. dissolved in 250 ml. water; 5 ml. equivalent to 6 lb/A preplant incorporated.

The crops tested were Navy bean - NB, Kidney bean - KB, Pinto bean - PB (various varieties of Phaeseolus vulgaris L.) and peas (Pisum sativum L.) The weed species included in the tests were watergrass - wg and foxtail - Ft.

TABLE V

| | | Percent Injury PPI (Tank Mix) 4 Week Data | | | |
|---|---|---|---|---|---|
| | | NB | PB | WG | FT |
| EPTC | 6 lb/A | 65 | 50 | 100 | 100 |
| COMPOUND | | | | | |

TABLE V-continued

| NUMBER | RATE | NB | PB | WG | FT |
|---|---|---|---|---|---|
| 3 | 1 lb/A | 30 | 20 | 100 | 100 |
|  | 2 lb/A | 20 | 20 | 100 | 100 |
| 17 | 1 lb/A | 30 | 50 | 100 | 100 |
|  | 2 lb/A | 50 | 40 | | |
| 18 | 1 lb/A | 25 | 30 | 100 | |
|  | 2 lb/A | 50 | 40 | | |
| 28 | 1 lb/A | 50 | 40 | | |
|  | 2 lb/A | 50 | 30 | 100 | 100 |
| 29 | 1 lb/A | 0 | 40 | 100 | 100 |
|  | 2 lb/A | 30 | 20 | 100 | 100 |
| 33 | 1 lb/A | 40 | 40 | 100 | 100 |
|  | 2 lb/A | 50 | 40 | 100 | 100 |
| 51 | 1 lb/A | 40 | 20 | 100 | 100 |
|  | 2 lb/A | 50 | 30 | 100 | 100 |
| 54 | 1 lb/A | 30 | 40 | 100 | 100 |
|  | 2 lb/A | 50 | 0 | 100 | 100 |
| 57 | 1 lb/A | 50 | 30 | 100 | 100 |
|  | 2 lb/A | 50 | 40 | 100 | 100 |
| 90 | 1 lb/A | 50 | 40 | 100 | 100 |
|  | 2 lb/A | 50 | 10 | 100 | 100 |

At two pounds for acre compound number 3 also exhibited complete protection (100%) of kidney leaves. Compound number 28 exhibited 50 percent protection of kidney beans at two pounds per acre. Injury to peas was decreased 37.5 percent with compound number 28 at two pounds per acre.

What is claimed is:

1. Compounds according to the formula

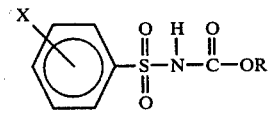

in which X is trifluoromethyl and R is haloalkyl having 2 to 6 carbon atoms, inclusive, and wherein halo is chloro or fluoro from 1 to 6, inclusive.

2. Compounds according to the formula

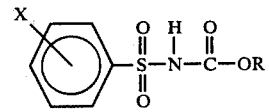

in which X is trifluoromethyl and R is alkenyl having 3 to 6 carbon atoms, inclusive.

3. Compounds according to the formula

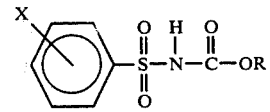

in which X is trifluoromethyl and R is alkynyl having 3 to 6 carbon atoms, inclusive.

* * * * *